United States Patent [19]

Richardson et al.

[11] Patent Number: 4,638,007

[45] Date of Patent: Jan. 20, 1987

[54] TRIAZOLE ANTIFUNGAL AGENTS

[75] Inventors: Kenneth Richardson; Peter J. Whittle, both of New York, N.Y.

[73] Assignee: Pfizer Inc., New York, N.Y.

[21] Appl. No.: 642,301

[22] Filed: Aug. 20, 1984

[30] Foreign Application Priority Data

Aug. 26, 1983 [GB] United Kingdom ............... 8322983

[51] Int. Cl.$^4$ ............... A61K 31/41; C07D 401/12; C07D 249/08
[52] U.S. Cl. ............... 514/340; 514/383; 546/276; 548/262
[58] Field of Search ............... 546/276; 548/262; 514/340, 383

[56] References Cited

U.S. PATENT DOCUMENTS

| | | | |
|---|---|---|---|
| 4,235,892 | 11/1980 | Nagabhushan | 424/226 |
| 4,311,857 | 1/1982 | Nagabhushan | 564/212 |
| 4,331,674 | 5/1982 | Kraimer et al. | 548/262 |
| 4,361,557 | 11/1982 | Nagabhushan | 424/226 |
| 4,399,143 | 8/1983 | Yokomichi et al. | 546/276 |
| 4,503,063 | 3/1985 | Richardson et al. | 546/276 |
| 4,518,604 | 5/1985 | Richardson et al. | 546/276 |

FOREIGN PATENT DOCUMENTS

| | | |
|---|---|---|
| 0061835 | 10/1982 | European Pat. Off. |
| 84834 | 8/1983 | European Pat. Off. |
| 85842 | 8/1983 | European Pat. Off. |
| 91309 | 10/1983 | European Pat. Off. |
| 95828 | 12/1983 | European Pat. Off. |
| 106515 | 4/1984 | European Pat. Off. |
| 113644 | 7/1984 | European Pat. Off. |
| 2908378 | 9/1980 | Fed. Rep. of Germany |
| 3018865 | 11/1981 | Fed. Rep. of Germany |
| 3202604 | 8/1983 | Fed. Rep. of Germany |
| 3202602 | 8/1983 | Fed. Rep. of Germany |
| 2101994 | 1/1983 | United Kingdom |

OTHER PUBLICATIONS

Burger Medicinal Chemistry 2nd Edition 1960, p. 1055.

*Primary Examiner*—Jane T. Fan
*Attorney, Agent, or Firm*—Charles J. Knuth; Albert E. Frost; Robert K. Blackwood

[57] ABSTRACT

Antifungal 1-[3-(substituted)-2-hydroxy-2-(perfluoroalkyl)-propyl]triazole derivatives wherein the 3-propyl substituent represents optionally substituted phenoxy, heteroaryloxy, alkylthio, alkylsulfinyl, alkylsulfonyl or optionally substituted carbamoyl.

21 Claims, No Drawings

TRIAZOLE ANTIFUNGAL AGENTS

BACKGROUND OF THE INVENTION

This invention relates to novel 1-[3-(substituted)-2-hydroxy(perfluoroalkyl)propyl]triazole derivatives which have antifungal activity and are useful in the treatment of fungal infections in animals, including humans, and as agricultural (including horticultural) fungicides.

European Patent Application No. 85,843 broadly discloses 1-propyltriazole antifungal agents of the formula $$\underset{N=N}{\overset{N}{\diagdown}}N-CH_2-\underset{R^a}{\overset{OR^b}{\underset{|}{C}}}-CH_2X^a$$

wherein the group $OR^b$ represents an ether functionality, $R^a$ includes "substituted alkyl" (specifically exemplified by a tertiary-butyl group), and $X^a$ includes optionally substituted phenoxy and phenylthio groups.

German Patent Documents Nos. 2,908,378 and 3,018,865 disclose antifungal agents which include compounds of the formula $$\underset{N=N}{\overset{N}{\diagdown}}N-CH_2-\underset{R^c}{\overset{OH}{\underset{|}{C}}}-CH_2X^b$$

wherein $R^c$ is hydrogen or alkyl and $X^b$ includes optionally substituted phenoxy and, when $R^c$ is hydrogen, also alkylthio.

European Patent Publications Nos. 95,828 and 106,515 describe antifungal agents of the formula $$\underset{N=N}{\overset{N}{\diagdown}}N-CH_2-\underset{R^d}{\overset{OH}{\underset{|}{C}}}-CH_2X^c$$

which include compounds wherein $R^d$ is optionally substituted phenyl and $X^c$ is alkylthio, alkylsulfinyl, alkylsulfonyl or substituted carbamoyl.

U.K. Patent Application No. 2,101,994 describes antifungal agents which include compounds of the formula $$\underset{N=N}{\overset{N}{\diagdown}}N-CH_2-\underset{R^e}{\overset{OH}{\underset{|}{C}}}\underset{}{\overset{CH_3}{\underset{|}{-CH}}}-X^d$$

wherein $R^e$ is alkyl and $X^d$ is optionally substituted phenoxy or phenylthio.

SUMMARY OF THE INVENTION

According to the invention, there are provided compounds of the formula:

$$\underset{N=N}{\overset{N}{\diagdown}}N-CH_2-\underset{(CF_2)_n}{\overset{OH}{\underset{|}{\underset{|}{C}}}}-CH_2-X \quad (I)$$
$$\underset{CF_3}{}$$

and their pharmaceutically and agriculturally acceptable salts, wherein n is zero or an integer of from 1 to 4; and X is selected from:

$$-O-\underset{R^2}{\bigotimes}-R^1 \quad (a)$$

where $R^1$ and $R^2$ are each independently H, F, Cl, Br, I, $CF_3$, $C_1$-$C_4$ alkyl, $C_1$-$C_4$ alkoxy, —CN or —$NO_2$; or $R^1$ is H and $R^2$ is 1,2,4-triazol-1-yl;

$$-O-Het \quad (b)$$

where "Het" is a 5- or 6-membered aromatic heterocyclic group containing at least one N atom and, optionally, one or two further heteroatoms each independently selected from N, S and O, and group "Het" being attached to the adjacent oxygen atom by a carbon atom and being optionally substituted by 1, 2 or 3 substituents each independently selected from F, Cl, Br, I, $CF_3$, $C_1$-$C_4$ alkyl and $C_1$-$C_4$ alkoxy;

$$-S(O)_m.(C_1\text{-}C_4 \text{ alkyl}) \quad (c)$$

where m is 0, 1 or 2; and $$-CONR^3R^4 \quad (d)$$

where $R^3$ and $R^4$ are each independently H or $C_1$-$C_4$ alkyl, or $R^3$ and $R^4$ taken together with the N atom to which they are attached represent a group of the formula:

$$-N\overset{}{\underset{}{\diagup\diagdown}}, -N\overset{}{\underset{}{\diagup\diagdown}}, -N\overset{}{\underset{}{\diagup\diagdown}}O \text{ or } -N\overset{}{\underset{}{\diagup\diagdown}}N-R^5$$

where $R^5$ is H, $C_1$-$C_4$ alkyl, $C_2$-$C_4$ alkanoyl or ($C_1$-$C_4$ alkoxy)carbonyl.

The invention further provides a pharmaceutical or agricultural composition comprising a compound of the formula (I), or a pharmaceutically or agriculturally acceptable salt thereof, together with a pharmaceutically or agriculturally acceptable diluent or carrier.

The invention yet further provides a compound of the formula (I), or a pharmaceutically acceptable salt thereof, for use in medicine, in particular for treating fungal infections in humans.

The invention also provides a method of treating a plant or seed having a fungal infection, which comprises contacting said plant or seed, or the locus thereof, with antifungally effective amount of said compound of the formula (I) or agriculturally acceptable salt thereof.

Particular examples of said group "Het" are pyridyl, pyrimidinyl and triazolyl which can optionally be substituted with the said substituent(s), especially with F, Cl, Br or I.

"Het" is preferably 5-chloropyrid-2-yl.

"n" is preferably 1, 2 or 3, and is most preferably 1 or 2.

$R^1$ and $R^2$ are in one aspect preferably each independently H, F, Cl, Br, I, $CF_3$, $C_1$-$C_4$ alkyl or $C_1$-$C_4$ alkoxy.

In the preferred compounds X is selected from:

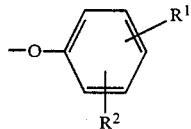
(a)

where $R^1$ and $R^2$ are each independently F, Cl, Br, I, —CN, or —$NO_2$; or $R^1$ is H and $R^2$ is 1,2,4-triazol-1-yl;

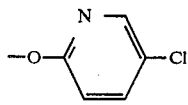
(b)

—$S(O)_n$-($C_1$-$C_4$alkyl) (c)

where n is 0 or 2; and

—$CONH_2$. (d)

More preferably, X is selected from 4-chlorophenoxy, 4-fluorophenoxy, 4-cyanophenoxy, 4-nitrophenoxy, 4-(1H-1,2,4-triazol-1-yl)phenoxy, 2,4-difluorophenoxy, 3,4-dichlorophenoxy, 5-chloropyrid-2-yloxy, methylthio, methylsulfonyl, and carbamoyl.

Most preferred groups represented by X include:

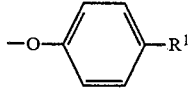
(a)

where $R^1$ is F, Cl, Br or I, preferably F or Cl;

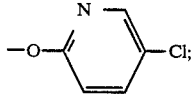
(b)

—$SO_2CH_3$; (c)

and

—$CONH_2$. (d)

DETAILED DESCRIPTION OF THE INVENTION

The compounds of the formula (I) in which X is said optionally substituted phenoxy group or is —O—Het can be prepared as follows:

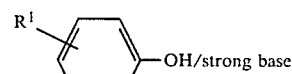

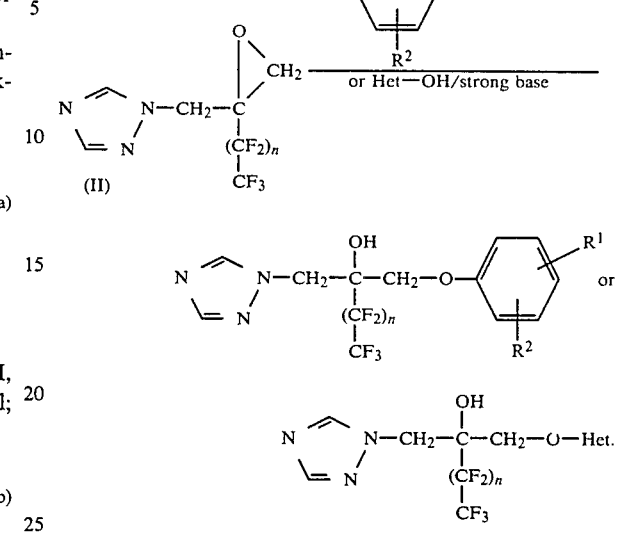

The preferred base is sodium hydride.

Thus in a typical procedure, the heteroaryl hydroxide or phenol in a suitable solvent, e.g. dimethylformamide (DMF) is slowly added with cooling to sodium hydride in DMF. After effervescence has ceased, usually in about 15 minutes, the epoxide (II) is added in e.g. DMF. The reaction will generally proceed to completion at room temperature, although the reaction mixture can if necessary be heated at, say, up to 60° C. to accelerate the reaction. The product can then be isolated and purified by conventional procedures.

The starting materials of the formula (II) can be prepared conventionally, e.g. as follows:

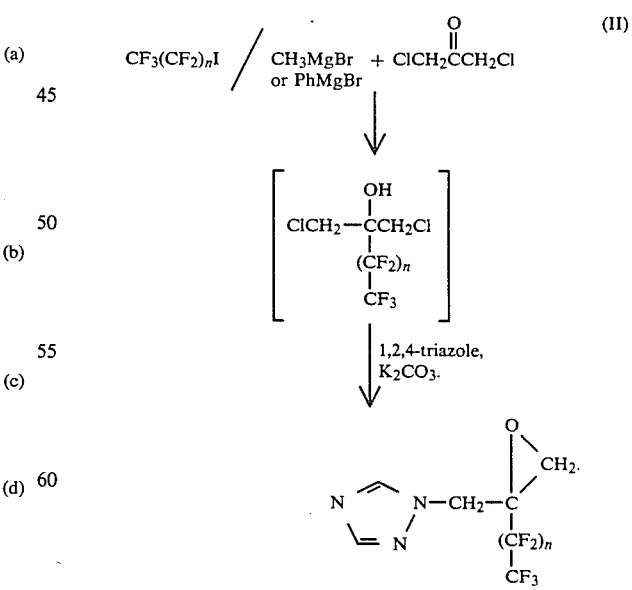

Details of typical experimental procedures for this process can be found in Examples 1, 12 and 14 hereinafter.

Compounds of the formula (I) in which X is —S(-$C_1$–$C_4$ alkyl) can be prepared according to the following reaction scheme:

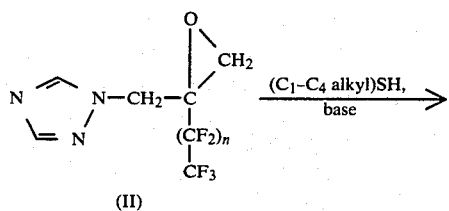

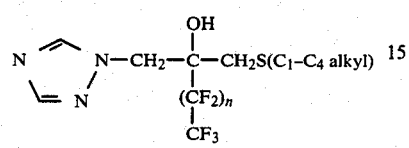

The preferred base is potassium carbonate. An alkali metal salt of the thiol can also be used.

In a typical procedure, the epoxide (II) and anhydrous potassium carbonate are stirred in a suitable solvent, e.g. dry dimethylformamide, followed by the addition of the alkanethiol.

The product can then be recovered conventionally.

Compounds in which X is

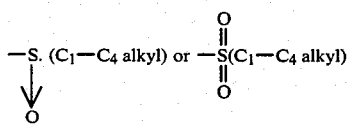

can be prepared by the oxidation of the corresponding sulphides using m-chloroperbenzoic acid in conventional manner.

The primary amides of the formula (I) can be prepared as follows:

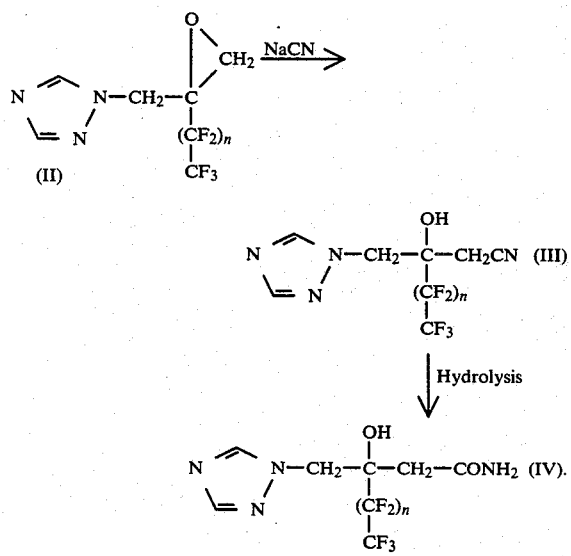

The reaction with sodium cyanide is typically carried out by stirring the reactants in aqueous dimethylformamide.

The hydrolysis is typically carried out by heating the nitrile at, say, 70°–100° C. with aqueous sulphuric acid, preferably 80% strength, for a short period, e.g. about 1 hour.

If desired, the hydrolysis can be continued under similar conditions to produce the corresponding acid which can then be used to prepare amides of the formula (I):

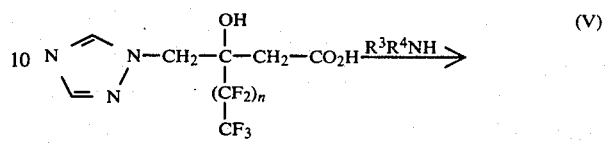

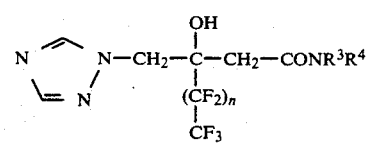

If compound (V) is reacted in its free acid form, the reaction should generally be carried out in the presence of a dehydrating agent such as dicyclohexylcarbodiimide.

Compound (V) is however preferably used in the form of its "functional equivalent as an acylating agent", e.g. as an acid chloride or bromide, a mixed anhydride of the formula:

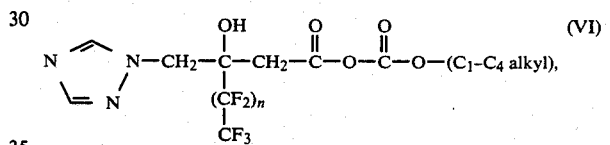

or as a $C_1$–$C_4$ alkyl, succinimido, phthalimido or benzotriazol-1-yl ester.

All these "functional equivalents" are preparable conventionally from the acid (V). The acid chlorides and bromides are for example preparable by reaction of said acid with thionyl chloride or bromide, the mixed anhydrides by reaction with a $C_2$–$C_5$ alkanoyl chloride, the $C_1$–$C_4$ alkyl esters by simple esterification, and the succinimido, phthalimido and benzotriazol-1-yl esters by reaction with N-hydroxysuccinimide, N-hydroxyphthalimide or 1-hydroxybenzotriazole in the presence of a dehydrating agent such as dicyclohexylcarbodiimide.

Particularly useful are the succinimido esters of the formula:

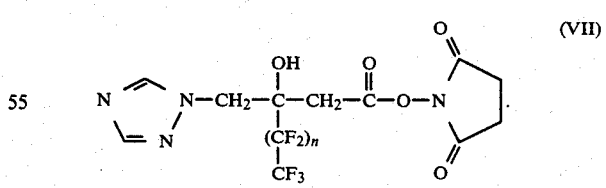

Thus in a typical procedure, dicyclohexylcarbodiimide dissolved in e.g. dry dioxan is added to a solution of the acid (V) and N-hydroxysuccinimide in e.g. dry dioxan. After stirring for a few hours at room temperature and filtering, the reaction is generally completed by stirring the solution of the compound (VII) with the amine $R^3R^4NH$ at room temperature for a few hours in e.g. dry dioxan, after which the product can be isolated and purified by conventional means.

The benzotriazol-1-yl esters are also particularly useful and have the formula:

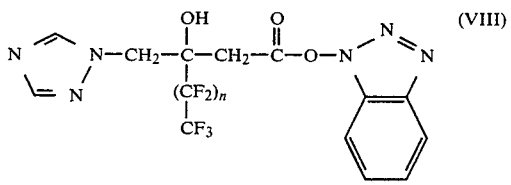

These can be prepared as stated above.

Thus in a typical procedure, dicyclohexylcarbodiimide, 1-hydroxybenzotriazole and the acid (V) are stirred together at room temperature for a short period in e.g. dry dioxan. The reaction is generally completed by stirring the resulting intermediate (VIII) with the amine $R^3R^4NH$ at room temperature until the reaction is complete, after which the product can be isolated and purified by conventional means.

Compounds in which X is —$CONH(C_1-C_4$ alkyl) or —$CON(C_1-C_4$ alkyl)$_2$ can be prepared by the alkylation of the corresponding starting materials in which X is —$CONH_2$. The alkylation is typically carried out by dissolving the starting material in a suitable organic solvent, e.g. dry THF, followed by cooling to 0°–5° C. A strong base such as sodium hydride is then added. After stirring for a few minutes, an appropriate quantity of alkylating agent is added. The preferred alkylating agents are the alkali metal iodides and bromides. For mono-alkylation, only one equivalent of alkylating agent should be used, and, for dialkylation, at least 2 equivalents. The alkylated product can be isolated from the reaction mixture by conventional techniques.

The compounds of the invention contain a chiral centre or centres and the invention includes both the resolved and unresolved forms.

Pharmaceutically and agriculturally acceptable acid addition salts of the compounds of the formula (I) are those formed from strong acids which form non-toxic acid addition salts, such as hydrochloric, hydrobromic, sulphuric, oxalic and methanesulphonic acids.

The salts may be obtained by conventional procedures, e.g. by mixing solutions containing equimolar amounts of the free base and desired acid, and the required salt is collected by filtration, if insoluble, or by evaporation of the solvent.

Also included are the alkali metal salts, preparable conventionally.

The compounds of the formula (I) and their pharmaceutically acceptable salts are antifungal agents, useful in combating fungal infections in animals, including humans. For example they are useful in treating topical fungal infections in man caused by, among other organisms, species of Candida, Trichophyton, Microsporum or Epidermophyton, or in mucosal infections caused by *Candida albicans* (e.g. thrush and vaginal candidiasis). They can also be used in the treatment of systemic fungal infections caused by, for example, *Candida albicans, Cryptococcus neoformans, Aspergillus fumigatus,* Coccidioides, Paracoccidioides, Histoplasma or Blastomyces.

The in vitro evaluation of the antifungal activity of the compounds can be performed by determining the minimum inhibitory concentration (m.i.c.) which is the concentration of the test compounds in a suitable medium at which growth of the particular micro-organism fails to occur. In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other micro-organisms used in such tests can include *Cryptococcus neoformans, Aspergillus fumigatus,* Trichophyton spp; Microsporum spp; *Epidermophyton floccosum, Coccidioides immitis* and *Torulopsis glabrata.*

The in vivo evaluation of the compounds can be carried out at a series of dose levels by intraperitoneal or intravenous injection or by oral administration, to mice which are inoculated with a strain of *Candida albicans.* Activity is based on the survival of a treated group of mice after the death of an untreated group of mice following 48 hours observation. The dose level at which the compound provides 50% protection ($PD_{50}$) against the lethal effect of the infection is noted.

For human use, the antifungal compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) will be from 0.1 to 5 mg/kg (in divided doses) when administered by either the oral or parenteral route. Thus tablets or capsules of the compounds will contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can; of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 an 10%, into an ointment consisting of a white wax or white soft paraffin base together with such stabilizers and preservatives as may be required.

The compounds of the formula (I) and their salts also have activity against a variety of plant pathogenic fungi, including for example various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Micro-organisms used in such tests include *Cochliobolus carbonum, Pyricularia oryzae, Glomerelld cingulata, Penicillium digitatum, Botrytis cinerea* and *Rhizoctonia solani.*

For agricultural and horticultural purposes the compounds and their agriculturally acceptable salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be applied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example they can be applied directly to the plant foilage, stems, branches, seeds or roots or to the soil or other growing medium, and they may be used not only to eradicate disease, but also prophylactically to protect the plants or seeds from attack.

The invention also includes the novel intermediates of the formulae (II) and (III).

The following Examples illustrate the invention. All temperatures are in °C:

EXAMPLE I

Preparation of
3,3,4,4,5,5,5-heptafluoro-1-(5-chloropyrid-2-yloxy)-2-(1H-1,2,4-triazol-1-ylmethyl)-pentam-2-ol below −65°. The mixture was then stirred at −30° (all the precipitate dissolved at this temperature) for 1 hour, and was quenched by the slow addition of a solution of ammonium chloride (∼4 g) in water (50 ml), and was stirred until the temperature reached about 5°. The phases were then separated and the aqueous phase was extracted with ether (2×100 ml). The organic extracts were combined, dried (MgSO$_4$) and evaporated in vacuo without heating.

The resulting residue was then stirred for about 25 minutes with 1,2,4-triazole (2.16 g; 0.0314M) and anhydrous potassium carbonate (10.6 g; 0.0785M) in dimethylformamide (80 ml), and the solution was then diluted with water (100 ml) and extracted with dichloromethane (3×100 ml). The organic extracts were washed with brine (200 ml), dried (MgSO$_4$) and evaporated in vacuo without heating, yielding the epoxide (IIA) in slightly impure form (1.6 g). The epoxide was used without purification. Sodium hydride (60% dispersion in oil; 230 mg; 0.00552M) was washed with dry ether, dried, and suspended in dry dimethylformamide (10 ml), and 5-chloro-2-hydroxypyridine (920 mg; 0.0069M) in dry dimethylformamide (20 ml) was slowly added with cooling. When effervescence had ceased and a clear solution was obtained (∼10 minutes), the epoxide (IIA) (1.6 g; 0.0054M) was added in dry dimethylformamide (20 ml), and the mixture was stirred at room temperature (20°) for 18 hours. The mixture was then diluted with water (200 ml) and extracted with dichloromethane (3×200 ml). The organic extracts were combined and washed with brine, dried (MgSO$_4$) and the solvent was evaporated in vacuo. The residue was purified by column chromatography on silica (230–400 mesh) eluting with ethylacetate/hexane (65/35% by volume). After evaporation of appropriate fractions, the product was recrystallised from methylene chloride/hexane yielding the pure title compound (75 mg) as a white solid, m.p. 81°–83°.

Analysis %: Found: C, 37.1; H, 2.4; N, 13.1; Calculated for C$_{13}$H$_{10}$F$_7$ClN$_4$O$_2$: C, 36.9; H, 2.4; N, 13.25.

EXAMPLES 2 TO 11

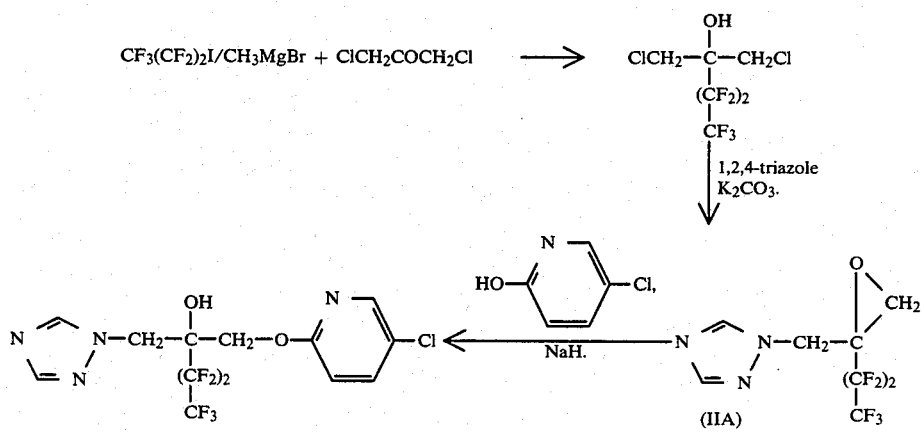

Heptafluoropropyliodide (11.12 g; 0.0376M) was stirred in dry ether (40 ml) at −75°. To this was added methylmagnesium bromide (11.44 ml of a 3M solution in ether; 0.0345M) dropwise with stirring, keeping the internal temperature at below −65°. This solution was stirred for 1 hour at −75°, followed by the dropwise addition of 1,3-dichloroacetone (4 g; 0.0314M) in dry ether (60 ml), maintaining the internal temperature at The following compounds were prepared simlarly to Example 1 from analogous starting materials:

| Example No. | n | X | m.p. (°C.) | Analysis % (Theoretical in brackets) C H N (or n.m.r.) |
|---|---|---|---|---|
| 2 | 2 | −O−⟨C6H4⟩−Cl | 82–83° | 39.6 2.5 10.1 (39.9 2.6 10.0) |
| 3 | 2 | −O−⟨C6H4⟩−F | 82–83° | 41.4 2.65 10.3 (41.5 2.7 10.4) |
| 4 | 2 | −O−⟨C6H4⟩−CN | 158–9° | 43.7 2.7 13.6 (43.7 2.7 13.6) |
| 5 | 1 | −O−⟨C6H4⟩−Cl | 84–86° | 42.0 3.0 11.3 (42.0 3.0 11.3) |
| 6 | 1 | −O−⟨C6H4⟩−F | 83–84° | 43.7 3.1 11.7 (43.95 3.1 11.8) |
| 7 | 1 | −O−⟨C6H4⟩−CN | 130–132° | 46.0 3.1 15.2 (46.4 3.0 15.4) |
| 8 | 1 | −O−⟨C6H4⟩−NO2 | 136–137° | 40.7 2.8 14.0 (40.8 2.9 14.6) |
| 9 | 1 | −O−⟨C6H4⟩−N(triazolyl) | 142–3° | 44.8 3.1 20.5 (44.6 3.2 20.8) |
| 10 | 1 | −O−⟨C6H3⟩(F)(F) | 85° | 41.7 2.7 11.3 (41.8 2.7 11.3) |
| 11 | 1 | −O−⟨C6H3⟩(Cl)(Cl) | 63–4° | N.m.r. (CDCl3). δ = 8.1 (s,1H); 7.9 (s,1H); 7.3 (d,J=8Hz,1H); 6.9 (d,J=3Hz, 1H); 6.65 (dd, J=8Hz,3Hz, 1H); 4.7 (s,2H); 4.1 (d,J=10Hz, 1H); 3.75 (d, J=10Hz,1H). |

EXAMPLE 12

Preparation of 1-methylthio-3,3,4,4,5,5,6,6,6-nonafluoro-2-(1H-1,2,4-triazol-1-ylmethyl)hexan-2-ol $CF_3(CF_2)_3I/PhMgBr + ClCH_2COCH_2Cl \longrightarrow$ (IIB)

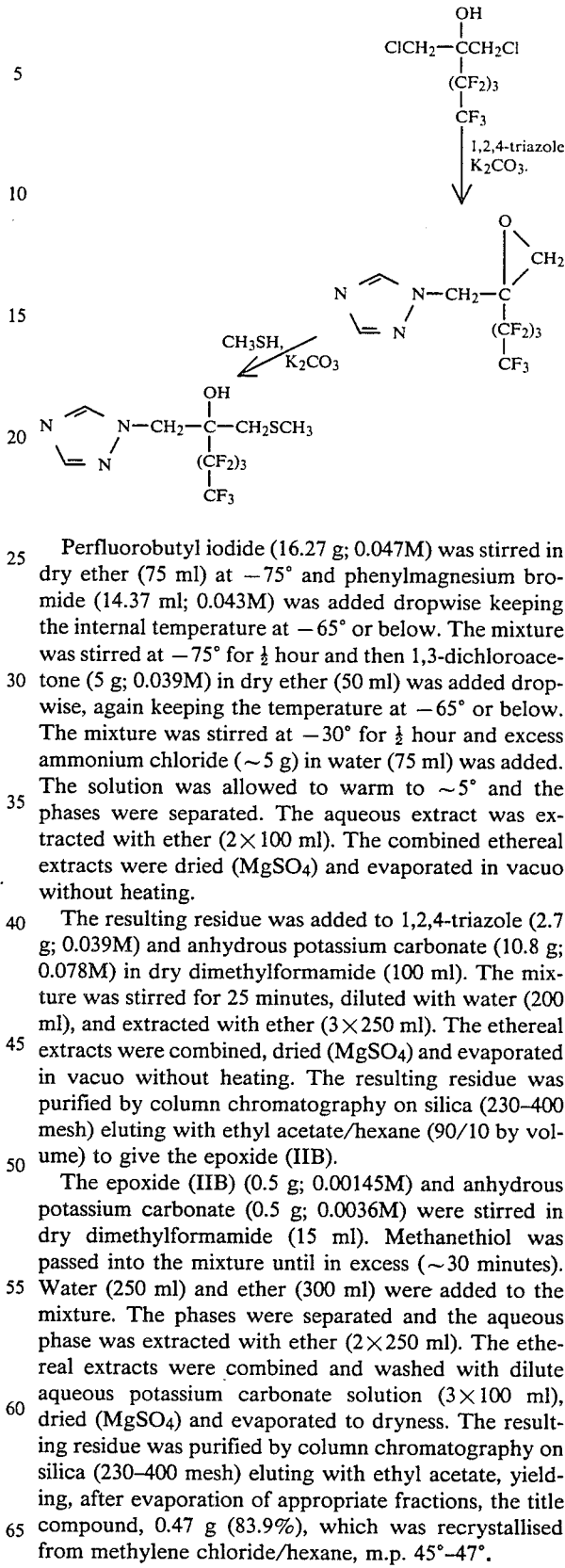

Perfluorobutyl iodide (16.27 g; 0.047M) was stirred in dry ether (75 ml) at −75° and phenylmagnesium bromide (14.37 ml; 0.043M) was added dropwise keeping the internal temperature at −65° or below. The mixture was stirred at −75° for ½ hour and then 1,3-dichloroacetone (5 g; 0.039M) in dry ether (50 ml) was added dropwise, again keeping the temperature at −65° or below. The mixture was stirred at −30° for ½ hour and excess ammonium chloride (~5 g) in water (75 ml) was added. The solution was allowed to warm to ~5° and the phases were separated. The aqueous extract was extracted with ether (2×100 ml). The combined ethereal extracts were dried (MgSO4) and evaporated in vacuo without heating.

The resulting residue was added to 1,2,4-triazole (2.7 g; 0.039M) and anhydrous potassium carbonate (10.8 g; 0.078M) in dry dimethylformamide (100 ml). The mixture was stirred for 25 minutes, diluted with water (200 ml), and extracted with ether (3×250 ml). The ethereal extracts were combined, dried (MgSO4) and evaporated in vacuo without heating. The resulting residue was purified by column chromatography on silica (230–400 mesh) eluting with ethyl acetate/hexane (90/10 by volume) to give the epoxide (IIB).

The epoxide (IIB) (0.5 g; 0.00145M) and anhydrous potassium carbonate (0.5 g; 0.0036M) were stirred in dry dimethylformamide (15 ml). Methanethiol was passed into the mixture until in excess (~30 minutes). Water (250 ml) and ether (300 ml) were added to the mixture. The phases were separated and the aqueous phase was extracted with ether (2×250 ml). The ethereal extracts were combined and washed with dilute aqueous potassium carbonate solution (3×100 ml), dried (MgSO4) and evaporated to dryness. The resulting residue was purified by column chromatography on silica (230–400 mesh) eluting with ethyl acetate, yielding, after evaporation of appropriate fractions, the title compound, 0.47 g (83.9%), which was recrystallised from methylene chloride/hexane, m.p. 45°–47°.

Analysis %: Found: C, 30.7; H, 2.6; N, 10.5; Calculated for $C_{10}H_{10}F_9N_3OS$: C, 30.7; H, 2.6; N, 10.7.

EXAMPLE 13

Preparation of
1-methylsulphonyl-3,3,4,4,5,5,6,6,6-nonafluoro-2-(1H-1,2,4-triazol-1-ylmethyl)hexan-2-ol

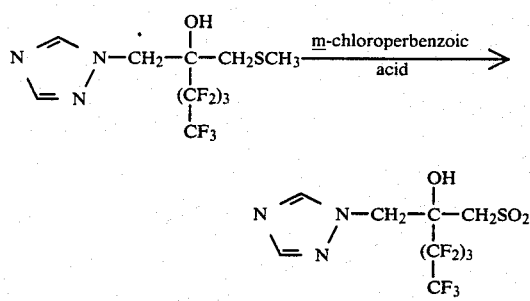

1-Methylthio-3,3,4,4,5,5,6,6,6-nonafluoro-2-(1H-1,2,4-triazol-1-ylmethyl)hexan-2-ol (0.3 g; 0.00076M) was dissolved in dry methylene chloride (10 ml) and the mixture was stirred with ice-cooling. Metachloroperbenzoic acid (407 mg; 0.0017M; based on 75% pure) was added portion-wise over 10 minutes and the mixture was stirred at room temperature (20°) overnight. The mixture was then diluted with methylene chloride (~40 ml) and was washed with 4×25 ml of a solution of sodium bicarbonate (2.0 g) and sodium metabisulphite (2 g) in water (100 ml). The organic phase was dried (MgSO₄) and the solvent was removed in vacuo. The residue was purified by column chromatography on silica (230–400 mesh) eluting with ethyl acetate. Evaporation of appropriate fractions and recrystallization of the residue from methylene chloride/hexane yielded the pure title compound, 126 mg, as a white solid (38.8%), m.p. 106°–9°.

Analysis %: Found: C, 28.6; H, 2.35; N, 10.1; Calculated for $C_{10}H_{10}F_9N_3O_3S$: C, 28.4; H, 2.4; N, 9.9.

EXAMPLE 14

Preparation of
3,3,4,4,5,5,5-heptafluoro-1-methylsulphony-2-(1H-1,2,4-triazol-1-ylmethyl)pentan-2-ol

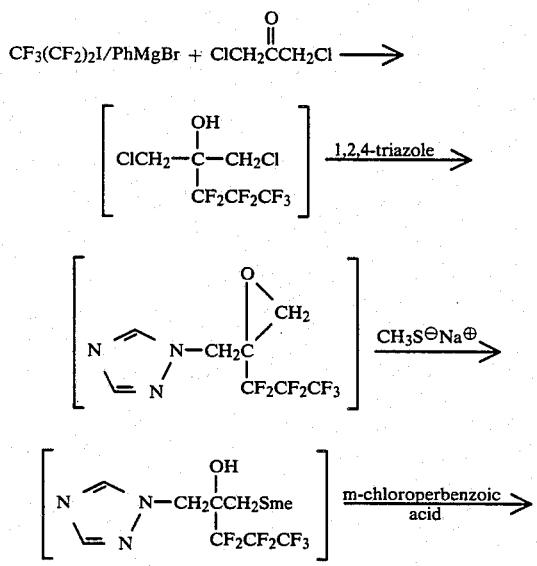

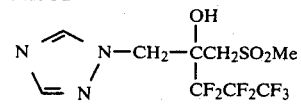

A solution of heptafluoropropyl iodide (14.58 g, 49.2 m.mole) in diethylether (65 ml) was stirred and cooled to −70°. A solution of phenylmagnesium bromide in diethylether (15.75 ml of a 3 molar solution; 47.25 m.mole) was then added dropwise at such a rate that the temperature of the reaction mixture did not exceed −65°. When the addition was complete, stirring was continued for 15 minutes and a solution of 1,3-dichloroacetone (5 g, 39.4 m.mole) in diethylether was then added dropwise, again at such a rate that the temperature of the reaction mixture did not exceed −65°. When the addition was complete, stirring was continued at −70° for 1 hour and then a saturated aqueous solution of ammonium chloride (50 ml) was added. The reaction mixture was allowed to warm to room temperature, water (25 ml) was added, and the aqueous layer was separated and extracted with diethylether (2×25 ml). The combined diethylether extracts were dried (MgSO₄) and evaporated to give a pale yellow liquid which was immediately added to a stirred mixture of 1,2,4-triazole (2.7 g, 39.4 m.mole), anhydrous potassium carbonate (10.8 g, 78.75 m.mole) and dimethylformamide (DMF) (125 ml). Stirring was continued for 2.5 hours at room temperature and the reaction mixture was then poured into a mixture of diethylether (250 ml) and brine (800 ml). The aqueous layer was separated and extracted with diethylether (2×50 ml) and the combined diethylether extracts were dried (MgSO₄) and evaporated. The residue was then flash chromatographed on silica (230–400 mesh), eluting with ethyl acetate to give, as a pale brown solid, 2-heptafluoropropyl-2-(1H-1,2,4-triazol-1-ylmethyl)oxirane (240 mg), which was used immediately in the next step.

The oxirane (240 mg, 0.82 m.mole) from the above preparation was stirred in DMF (10 ml) with anhydrous potassium carbonate (340 mg, 2.5 m.mole), and methanethiol was slowly bubbled through the reaction mixture until the starting oxirane had been consumed. The reaction mixture was then poured into a mixture of diethylether (200 ml) and dilute potassium carbonate solution (100 ml) and the aqueous layer was separated. The diethylether layer was washed further with potassium carbonate solution (6×50 ml) and the combined aqueous washings were extracted with diethylether (2×50 ml). The combined diethylether extracts were dried (MgSO₄) and evaporated to give a yellow gum (310 mg) which was dissolved in dichloromethane (10 ml). The solution was cooled in ice and metachloroperbenzoic acid (0.311 g, 1.8 m.mole) was added portion-wise over 5 minutes. The solution was allowed to warm to room temperature and stirred for 18 hours. Dichloromethane (5 ml) was then added followed by dilute sodium metabisulphite solution (10 ml) and saturated sodium bicarbonate solution (10 ml). The organic layer was separated and washed once with saturated sodium bicarbonate solution. The combined aqueous fractions were extracted with dichloromethane (4×20 ml) and the combined extracts were dried (MgSO₄) and evaporated to give a white solid which was flash chromatographed on silica (270–400 mesh), eluting with ethyl acetate to give, after evaporation of appropriate fractions, the title compound as a white solid, 220 mg; (1.5%, based on dichloroacetone), m.p. (after recrystallisation from ethyl acetate/hexane) 164°–165°.

Analysis %: Found: C, 29.1; H, 2.7; N, 11.3; Calculated for $C_9H_{10}F_7N_3O_3S$: C, 29.0; H, 2.7; N, 11.3.

EXAMPLE 15

Preparation of 1-carbamoyl-3,3,4,4,5,5,6,6,6-nonafluoro-2-(1H-1,2,4-triazol-1-ylmethyl)hexan-2-ol

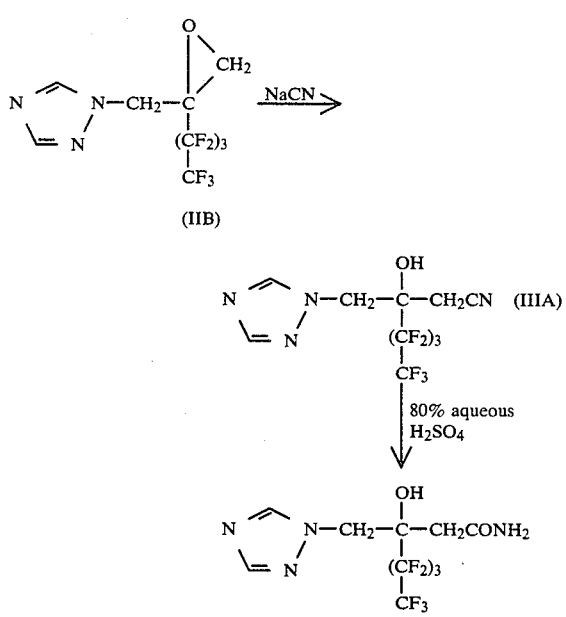

The epoxide (IIB) (0.5 g; 0.00145M), sodium cyanide (0.14 g; 0.0029M) and 10% aqueous dimethylformamide (12 ml) were stirred together for 1 hour. Brine (100 ml) and ethylacetate (100 ml) were added and the phases were separated. The organic phase was washed with brine (6×25 ml), dried (MgSO$_4$) and evaporated in vacuo. The residue was purified by column chromatography on silica (230–400 mesh) eluting with ethylacetate. After collection and evaporation of appropriate fractions, the resulting material was triturated with hexane to give a white solid which was recrystallised from methylene chloride/hexane to give 140 mg (26.4%) of the pure nitrile (IIIA), m.p. 101°–2°.

Analysis %: Found: C, 32.2; H, 1.8; N, 14.8; Calculated for $C_{10}H_7F_9N_4O$: C, 32.4; H, 1.9; N, 15.1.

The nitrile (IIIA) (0.10 g; 0.00027M) and 80% by volume aqueous sulphuric acid (3 ml) were stirred together at 90° for 1 hour. The mixture was then cooled in ice and poured into a mixture of water (30 ml) and methylene chloride (20 ml). Excess acid was then neutralized by the addition of solid sodium bicarbonate. The phases were separated and the aqueous phase was washed with methylene chloride (6×20 ml). The organic extracts were combined, dried (MgSO$_4$) and evaporated in vacuo. The residue was purified by column chromatography on silica (230–400 mesh) eluting with 2% methanol in ethylacetate. After collection and evaporation of appropriate fractions, the resulting white solid was recrystallized from ethylacetate/hexane, yielding pure title compound, 17 mg (16.3%), m.p. 145°–6°.

Analysis %: Found: C, 31.2; H, 2.3; N, 14.4; Calculated for $C_{10}H_9F_9N_4O_2$: C, 30.9; H, 2.3; N, 14.4.

EXAMPLE 16

(A.) Preparation of 1-cyano-3,3,4,4,5,5,5-heptafluoro-2-(1H-1,2,4-triazol-1-ylmethyl)pentan-2-ol

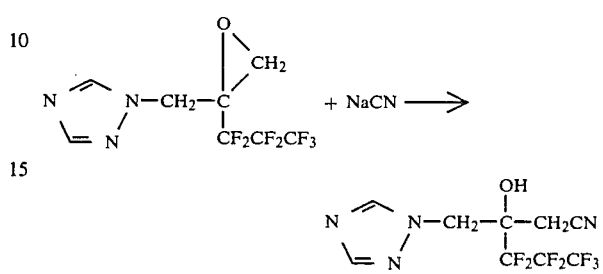

2-Heptafluoropropyl-2-(1H-1,2,4-triazol-1-ylmethyl)oxirane (390 mg, 1.33 m.mole) and sodium cyanide (130 mg, 2.66 m.mole) were stirred together at room temperature in a mixture of dimethylformamide (9 ml) and water (1 ml) for 20 hours. The reaction mixture was then partitioned between ethyl acetate (100 ml) and brine (100 ml) and the aqueous layer was separated. The organic layer was washed further with brine (6×25 ml) and the combined aqueous extracts were extracted with ethyl acetate (2×25 ml). The combined organic extracts were dried (MgSO$_4$) and evaporated and the residual gum (450 mg) was flash chromatographed on silica (230–400 mesh), eluting with 85:15 dichloromethane:methanol to give a pale yellow gum which was flash chromatographed on silica (230–400 mesh), eluting with 93:7:1, dichloromethane:methanol:0.88 ammonium hydroxide, to give after evaporation of appropriate fractions the title compound, 356 mg (69%), m.p. (after recrystallisation from hexane/dichloromethane) 92°–93°.

Analysis %: Found: C, 33.9; H, 2.1; N, 17.6; Calculated for $C_9H_7F_7N_4O$: C, 33.75; H, 2.2; N, 17.5.

(B.) Preparation of 1-carbamoyl-4,4,5,5,6,6,6-heptafluoro-2-(1H-1,2,4-triazol-1-ylmethyl)pentan-2-ol

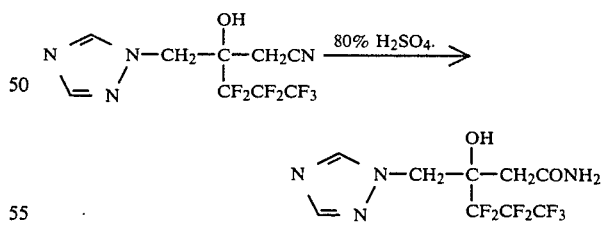

1-Cyano-3,3,4,4,5,5,5-heptafluoro-2-(1H-1,2,4-triazol-1-ylmethyl)pentan-2-ol (256 mg, 0.76 m.mole) was stirred at 90° in 80% sulphuric acid for 1 hour. The solution was then cooled in ice/water and poured into a mixture of water (50 ml) and dichloromethane (30 ml). The mixture was then neutralised with solid sodium bicarbonate, the aqueous layer was saturated with salt, and the organic layer was separated. The aqueous layer was extracted further with dichloromethane (5×20 ml) and ethyl acetate (2×25 ml) and the combined organic extracts were dried (MgSO$_4$) and evaporated to give a white solid (180 mg) which was flash chromatographed on silica (230–400 mesh), eluting with 95:5 ethyl acetate:methanol to give the title compound 163 mg (60%), m.p. (after recrystallisation from ethyl acetate/hexane) 170°–171°.

Analysis %: Found: C, 31.9; H, 2.65; N, 16.6; Calculated for $C_9H_9F_7N_4O_2$: C, 31.95; H, 2.7; N, 16.6.

Activity Data $PD_{50}$ values (oral) against *Candida albicans* in mice after 48 hours for the compounds of the Examples are as follows:

| Compound | $PD_{50}$ (mg./kg) |
| --- | --- |
| Product of Example No. 1 | <1 |
| Product of Example No. 2 | <1 |
| Product of Example No. 3 | <1 |
| Product of Example No. 4 | 3.1 |
| Product of Example No. 5 | <1 |
| Product of Example No. 6 | <1 |
| Product of Example No. 7 | 4.2 |
| Product of Example No. 8 | 2.2 |
| Product of Example No. 9 | 4.2 |
| Product of Example No. 10 | 2.2 |
| Product of Example No. 11 | 1.6 |
| Product of Example No. 14 | 2.2 |
| Product of Example No. 15 | 2.2 |
| Product of Example No. 16 | 1.6 |

The preferred individual compounds are the products of Examples 1, 2, 3, 5 and 6.

We claim:

1. A compound having the formula

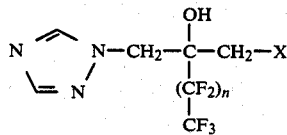

or a pharmaceutically or agriculturally acceptable salt thereof, wherein n is zero or an integer of from 1 to 4; and X is:

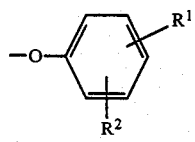 (a)

where $R^1$ and $R^2$ are each independently H, F, Cl, Br, I, $CF_3$, $C_1$–$C_4$ alkyl, $C_1$–$C_4$ alkoxy, —CN or —$NO_2$; or $R^1$ is H and $R^2$ is 1,2,4-triazol-1-yl;

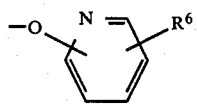 (b)

where $R^6$ is H, F, Cl, Br, I, $CF_3$, $C_1$–$C_4$ alkyl, $C_1$–$C_4$ alkoxy, —CN or —$NO_2$;

$S(O)_m(C_1–C_4$ alkyl) (c)

where m is 0, 1 or 2; or

—$CONR^3R^4$ (d)

where $R^3$ and $R^4$ are each independently H or $C_1$–$C_4$ alkyl.

2. A compound of claim 1 wherein n is 1, 2 or 3; X is

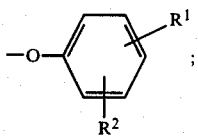

and $R^1$ and $R^2$ are each independently F, Cl, Br, I, —CN or —$NO_2$; or $R^1$ is H and $R^2$ is 1,2,4-triazol-1-yl.

3. A compound of claim 2, wherein X is 4-chlorophenoxy, 4-fluorophenoxy, 4-cyanophenoxy, 4-nitrophenoxy, 4-(1H-1,2,4-triazol-1-yl)phenoxy, 2,4-difluorophenoxy or 3,4-dichlorophenoxy.

4. The compound of claim 3 wherein n is 1 and X is 4-chlorophenoxy.

5. The compound of claim 3 wherein n is 2 and X is 4-chlorophenoxy.

6. The compound of claim 3 wherein n is 1 and X is 4-fluorophenoxy.

7. The compound of claim 3 wherein n is 2 and X is 4-fluorophenoxy.

8. A compound of claim 1 wherein n is 1, 2 or 3 and X is

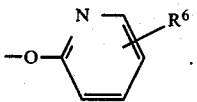

9. The compound of claim 8 wherein n is 2 and X is 5-chloropyrid-2-yloxy.

10. A compound of claim 1 wherein n is 1, 2 or 3 and X is —$S(O)_m(C_1$–$C_4$ alkyl).

11. The compound of claim 10 wherein n is 3 and X is methylthio.

12. The compound of claim 10 wherein n is 3 and X is methanesulfonyl.

13. The compound of claim 10 wherein n is 2 and X is methanesulfonyl.

14. A compound of claim 10 wherein n is 3 and X is methanesulfonyl.

15. A compound of claim 1 wherein n is 1, 2 or 3 and X is —$CONR^3R^4$.

16. The compound of claim 15 wherein n is 2 and X is —$CONH_2$.

17. The compound of claim 15 wherein n is 3 and X is —$CONH_2$.

18. A pharmaceutical composition comprising an antifungally effective amount of a compound of claim 1 together with a pharmaceutically acceptable diluent or carrier.

19. A method of treating a fungal infection in an animal, including man, which comprises administration of an antifungally effective amount of compound of claim 1.

20. A fungicidal composition for agricultural use, comprising an antifungally effective amount of a compound of claim 1 together with an agriculturally acceptable diluent or carrier.

21. A method of treating a plant or seed having a fungal infection, which comprises contacting said plant or seed, or the locus thereof, with an antifungally amount of a compound of claim 1.

* * * * *